US011344446B2

(12) United States Patent
Taylor et al.

(10) Patent No.: US 11,344,446 B2
(45) Date of Patent: May 31, 2022

(54) THERMAL SYSTEM WITH STEP RESPONSE

(71) Applicant: Stryker Corporation, Kalamazoo, MI (US)

(72) Inventors: Gregory S. Taylor, Kalamazoo, MI (US); Marko N. Kostic, Johnson City, TN (US); David Bowling, Los Ranchos, NM (US); Gregory Paul Starr, Albuquerque, NM (US)

(73) Assignee: Stryker Corporation, Kalamazoo, MI (US)

( * ) Notice: Subject to any disclaimer, the term of this patent is extended or adjusted under 35 U.S.C. 154(b) by 616 days.

(21) Appl. No.: 16/291,358

(22) Filed: Mar. 4, 2019

(65) Prior Publication Data
US 2019/0269547 A1 Sep. 5, 2019

Related U.S. Application Data

(60) Provisional application No. 62/638,400, filed on Mar. 5, 2018.

(51) Int. Cl.
*A61F 7/00* (2006.01)
*A61F 7/08* (2006.01)

(52) U.S. Cl.
CPC .......... *A61F 7/0085* (2013.01); *A61F 7/0097* (2013.01); *A61F 7/08* (2013.01);
(Continued)

(58) Field of Classification Search
CPC ...... A61F 2007/0018; A61F 2007/0039; A61F 2007/0054; A61F 2007/0093;
(Continued)

(56) References Cited

U.S. PATENT DOCUMENTS

2009/0112298 A1  4/2009  Jusiak et al.
2009/0240312 A1*  9/2009  Koewler .................. A61F 7/02
                                                   607/104
(Continued)

OTHER PUBLICATIONS

Gaymar Medi-Therm III, Hyper/Hypothermia Machine Ref MTA7912 Service Manual, Nov. 2009.
(Continued)

*Primary Examiner* — Tigist S Demie
(74) *Attorney, Agent, or Firm* — Warner Norcross + Judd LLP

(57) ABSTRACT

A thermal control unit for controlling a patient's temperature includes a fluid outlet for delivering temperature-controlled fluid to a patient, a pump, a heat exchanger, and a controller that automatically implements a step change in the temperature of the fluid delivered to the patient. The step change is implemented prior to the patient reaching a target patient temperature. In the moments after (and in some cases the moments before) the step change, the controller monitors the rate of change of patient's temperature to evaluate whether the patient will reach the target patient temperature without reversing the step change, and/or how long it will likely take for the patient to reach the target patient temperature without reversing the step change. The controller then determines whether to reverse the step change or to switch to another algorithm for controlling the fluid temperature.

19 Claims, 6 Drawing Sheets

(52) U.S. Cl.
CPC ............... *A61F 2007/0054* (2013.01); *A61F 2007/0093* (2013.01); *A61F 2007/0095* (2013.01)

(58) Field of Classification Search
CPC ...... A61F 2007/0095; A61F 2007/0295; A61F 7/0085; A61F 7/0097; A61F 7/02; A61F 7/08
See application file for complete search history.

(56) References Cited

U.S. PATENT DOCUMENTS

| | | |
|---|---|---|
| 2017/0348144 A1 | 12/2017 | Taylor et al. |
| 2017/0348449 A1 | 12/2017 | Ward et al. |
| 2018/0014967 A1 | 1/2018 | Taylor |
| 2018/0042762 A1 | 2/2018 | Galer |
| 2018/0042763 A1 | 2/2018 | Galer et al. |
| 2018/0098878 A1 | 4/2018 | Kostic et al. |
| 2018/0140459 A1 | 5/2018 | Taylor et al. |
| 2018/0214301 A1 | 8/2018 | Fojtik et al. |
| 2018/0280191 A1 | 10/2018 | Taylor et al. |

OTHER PUBLICATIONS

Altrix Precision Temperature Management System Stryker Operations Manuel, Dec. 2016.
Sorin Group, Heater-Cooling System 3T, Operating Instructions, 2015.
Arctic Sun 5000 Service Manual by Medivance, Inc., 2010-2011.

\* cited by examiner

THERMAL SYSTEM WITH STEP RESPONSE

CROSS-REFERENCE TO RELATED APPLICATIONS

This application claims priority to U.S. provisional patent application Ser. No. 62/638,400 filed Mar. 5, 2018, by inventors Gregory S. Taylor et al. and entitled THERMAL SYSTEM WITH STEP RESPONSE, the complete disclosure of which is incorporated herein by reference.

BACKGROUND

The present disclosure relates to a thermal control system for controlling the temperature of circulating fluid that is delivered to one or more thermal pads or catheters positioned in contact with a patient.

Thermal control systems are known in the art for controlling the temperature of a patient by providing a thermal control unit that supplies temperature-controlled fluid to one or more thermal pads or catheters positioned in contact with a patient. The thermal control unit includes one or more heat exchangers for controlling the temperature of the fluid and a pump that pumps the temperature-controlled fluid to the pad(s) and/or catheter. After passing through the pad(s) and/or catheter, the fluid is returned to the thermal control unit where any necessary adjustments to the temperature of the returning fluid are made before being pumped back to the pad(s) and/or catheter. In some instances, the temperature of the fluid is controlled to a static target temperature, while in other instances the temperature of the fluid is varied as necessary in order to automatically effectuate a target patient temperature.

The thermal control unit can be used to warm or cool a patient, and it is often desirable to heat or cool the patient to a target temperature relatively quickly. However, it is also often desirable to heat or cool the patient to a target temperature without significantly overshooting the target temperature.

SUMMARY

The present disclosure is directed to an improved thermal control unit that brings the patient's temperature to a target temperature in an expeditious manner while also simultaneously reducing any overshoot in the patient's temperature. By reducing such overshoot, the magnitude of oscillations in the patient's temperature above and below a target temperature may also be reduced, thereby enabling the patient's temperature to be maintained within a tighter range of the target temperature. Still other improved aspects of the thermal control system disclosed herein will be apparent to those skilled in the art in light of the following written description.

According to one embodiment of the present disclosure a thermal control unit is provided for controlling a patient's temperature that includes a fluid outlet, a fluid inlet, a circulation channel, a pump, a heat exchanger, a fluid temperature sensor, a patient temperature probe port, a user interface, and a controller. The circulation channel is fluidly coupled to the fluid outlet and fluid inlet. The pump circulates fluid through the circulation channel from the fluid inlet to the fluid outlet and out of the fluid outlet. The heat exchanger adds or removes heat from the fluid circulating in the circulation channel. The fluid temperature sensor senses a temperature of the circulating fluid. The patient temperature probe port receives patient temperature readings from a patient temperature probe. The user interface receives a patient target temperature, and the controller is adapted to send commands to the heat exchanger to control a temperature of the fluid during an initial time period and to implement a step change in the temperature of the fluid during a subsequent time period. The controller is further adapted to monitor a slope of the patient temperature readings during the subsequent time period.

According to other aspects of the disclosure, the controller is further adapted to monitor a slope of the patient temperature readings prior to implementing the step change.

In some embodiments, the subsequent time period lasts for a fixed amount of time.

The controller is adapted, in some embodiments, to maintain a substantially constant fluid target temperature during the subsequent time period.

According to some aspects, the controller is adapted to reverse the step change if the slope of the patient temperature readings changes by more than a threshold during the subsequent time period, and to not reverse the step change if the slope of the patient temperature readings does not change by more than the threshold during the subsequent time period.

The controller is further adapted in some embodiments to implement a second step change after the patient temperature has moved closer to the patient target temperature than it was when the first step change was implemented by the controller.

In some embodiments, the controller may further be adapted to control the heat exchanger using a first control loop feedback mechanism during the initial time period. The first control loop feedback mechanism uses a first set of coefficients and an error value defined as a difference between a current patient temperature reading and the patient target temperature. In such embodiments, the controller may further be adapted to use a second control loop feedback mechanism if the slope of the patient temperature readings does not change by more than a threshold during the subsequent time period. The second control loop feedback mechanism uses a second set of coefficients and the error value. The second set of coefficients includes at least one coefficient having a value different from a corresponding coefficient value in the first set of coefficients.

The controller is adapted, in some embodiments, to determine whether or not to reverse the step change based upon changes in the slope of the patient temperature readings during the subsequent time period. Alternatively, or additionally, the controller may determine whether or not to reverse the step change by determining a likelihood of the patient temperature readings reaching the target temperature without reversing the step change.

In some embodiments, the controller is adapted to implement the step change when the patient temperature readings reach a specific temperature, the specific temperature being defined with respect to the target temperature.

The controller may further be adapted to implement a second step change at a moment occurring after the subsequent time period. The second step change may occur when the patient temperature readings reach a second specific temperature that is closer to the patient target temperature than the patient temperature readings were when the first step change was implemented.

According to another embodiment of the present disclosure, a thermal control unit is provided that includes a fluid outlet, a fluid inlet, a circulation channel, a pump, a heat exchanger, a fluid temperature sensor, a patient temperature probe port, a user interface, and a controller. The circulation channel is fluidly coupled to the fluid outlet and fluid inlet.

The pump circulates fluid through the circulation channel from the fluid inlet to the fluid outlet and out of the fluid outlet. The heat exchanger adds or removes heat from the fluid circulating in the circulation channel. The fluid temperature sensor senses a temperature of the circulating fluid. The patient temperature probe port receives patient temperature readings from a patient temperature probe. The user interface receives a patient target temperature, and the controller is adapted to perform the following:

(a) during an initial time period, use a first control loop feedback mechanism to determine a target temperature for the fluid;

(b) during an interim time period, change a temperature of the fluid to an interim target fluid temperature not determined by the first control loop feedback mechanism;

(c) monitor a slope of the patient temperature readings during the interim time period; and (d) determine from the slope of the patient temperature readings whether to resume using the first control loop feedback mechanism or to switch to using a second control loop feedback mechanism during a subsequent time period, the subsequent time period occurring after the interim time period.

According other aspects of the present disclosure, if the slope of the patient temperature readings does not change by more than a threshold during the interim time period, the controller is adapted to switch to using the second control loop feedback mechanism. In addition, if the slope of the patient temperature readings does change by more than the threshold during the interim time period, the controller is adapted to switch back to using the first control loop feedback mechanism.

In some embodiments, the controller is further adapted to determine and record a slope of the patient temperature readings prior to the interim time period and to use the recorded slope when determining whether to resume using the first control loop mechanism or to switch to using the second control loop feedback mechanism.

The interim time period may last for a fixed amount of time.

In some embodiments, the controller starts the interim time period when the patient temperature readings reach a specific temperature that is defined with respect to the target temperature. In some embodiments, the controller selects an interim target fluid temperature that differs by at least five degrees Celsius from a target fluid temperature that is set by the first control loop feedback mechanism at an end of the initial time period.

The controller may be adapted to maintain the interim target fluid temperature at a substantially constant value throughout the interim time period.

Before the various embodiments disclosed herein are explained in detail, it is to be understood that the claims are not to be limited to the details of operation or to the details of construction, nor to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
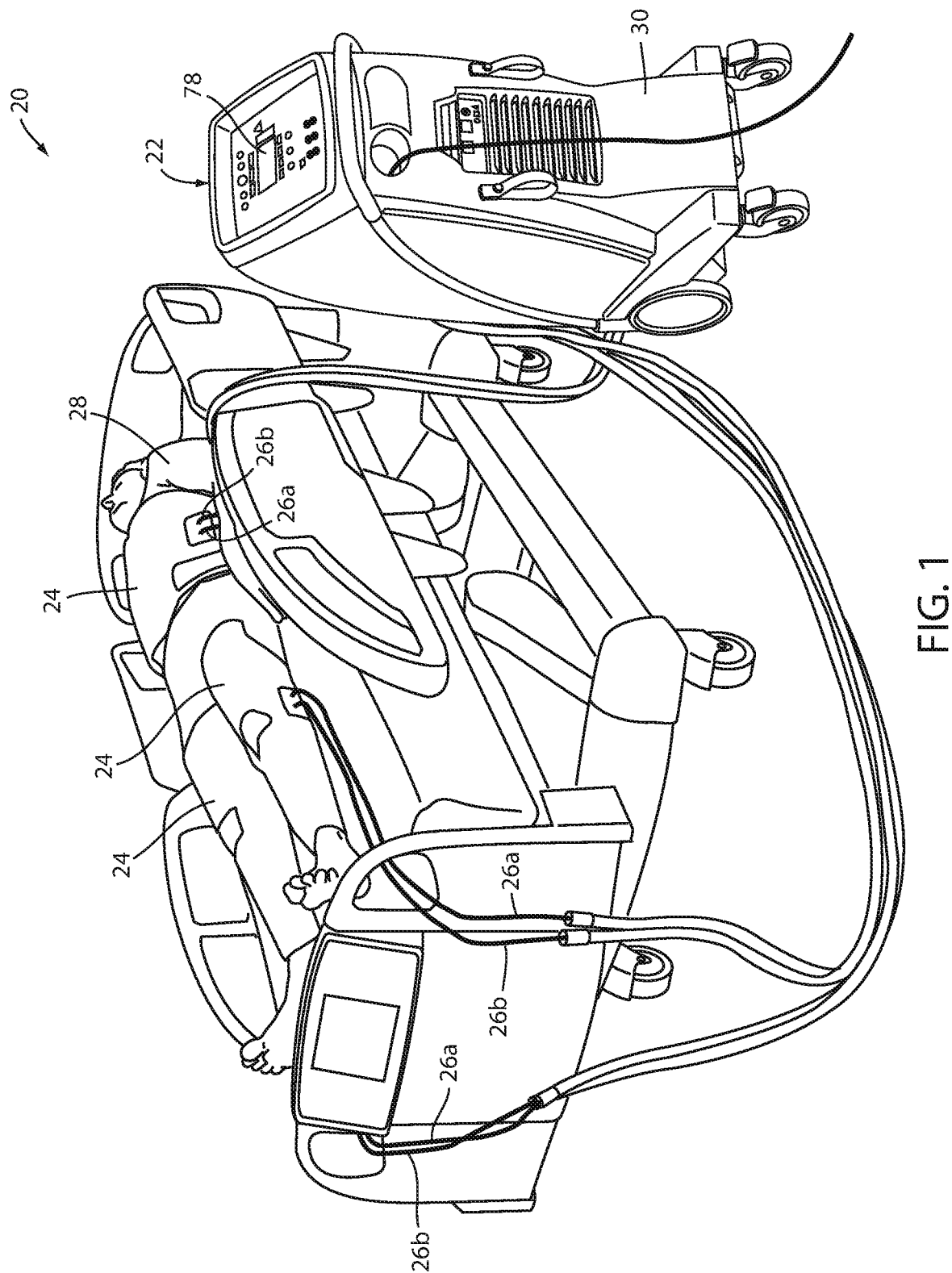
FIG. 1 is a perspective view of a thermal control system according to one aspect of the present disclosure shown applied to a patient on a patient support apparatus.

A thermal control system 20 according to one embodiment of the present disclosure is shown in FIG. 1. Thermal control system 20 is adapted to control the temperature of a patient 28, which may involve raising, lowering, and/or maintaining the patient's temperature. Thermal control system 20 includes a thermal control unit 22 coupled to one or more thermal therapy devices 24. The thermal therapy devices 24 are illustrated in FIG. 1 to be thermal pads, but it will be understood that thermal therapy devices 24 may take on other forms, such as, but not limited to, blankets, vests, patches, caps, catheters, or other structures that receive temperature-controlled fluid. For purposes of the following written description, thermal therapy devices 24 will be referred to as thermal pads 24, but it will be understood by those skilled in the art that this terminology is used merely for convenience and that the phrase "thermal pad" is intended to cover all of the different variations of thermal therapy devices 24 mentioned above (e.g. blankets, vests, patches, caps, catheters, etc.) and variations thereof.

Thermal control unit 22 is coupled to thermal pads 24 via a plurality of hoses 26. Thermal control unit 22 delivers temperature-controlled fluid (such as, but not limited to, water or a water mixture) to the thermal pads 24 via the fluid supply hoses 26a. After the temperature-controlled fluid has passed through thermal pads 24, thermal control unit 22 receives the temperature-controlled fluid back from thermal pads 24 via the return hoses 26b.

In the embodiment of thermal control system 20 shown in FIG. 1, three thermal pads 24 are used in the treatment of patient 28. A first thermal pad 24 is wrapped around a patient's torso, while second and third thermal pads 24 are wrapped, respectively, around the patient's right and left legs. Other configurations can be used and different numbers of thermal pads 24 may be used with thermal control unit 22, depending upon the number of inlet and outlet ports that are included with thermal control unit 22. By controlling the temperature of the fluid delivered to thermal pads 24 via supply hoses 26a, the temperature of the patient 28 can be controlled via the close contact of the pads 24 with the patient 28 and the resultant heat transfer therebetween.

Figure 2:
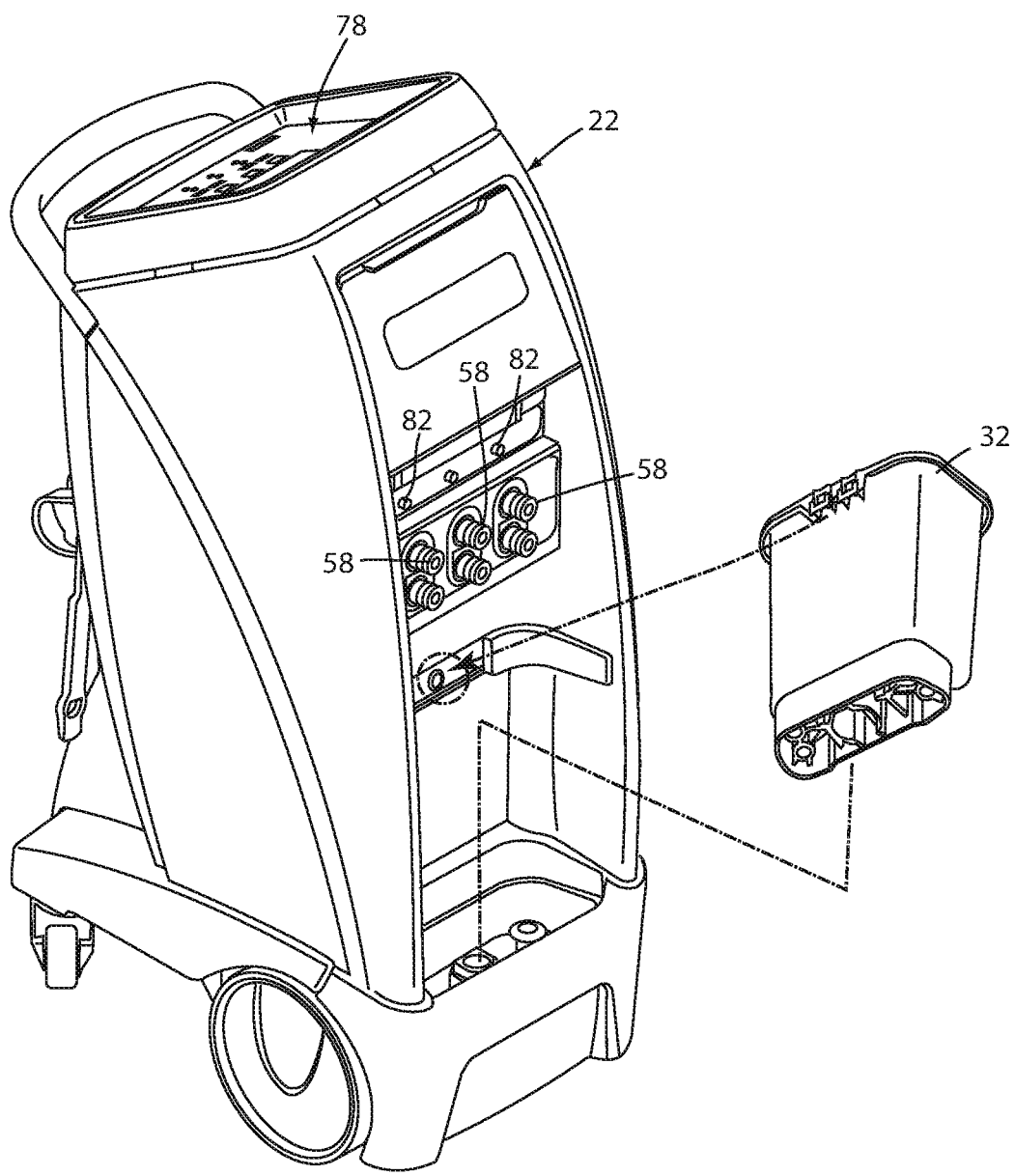
FIG. 2 is a perspective view of a thermal control unit of the thermal control system of FIG. 1.

As shown more clearly in FIG. 2, thermal control unit 22 includes a main body 30 to which a removable reservoir 32 may be coupled and uncoupled. Removable reservoir 32 is configured to hold the fluid that is to be circulated through control unit 22 and the one or more thermal pads 24. By being removable from thermal control unit 22, reservoir 32 can be easily carried to a sink or faucet for filling and/or dumping of the water or other fluid. This allows users of thermal control system 20 to more easily fill control unit 22 prior to its use, as well as to drain unit 22 after use.

Figure 3:
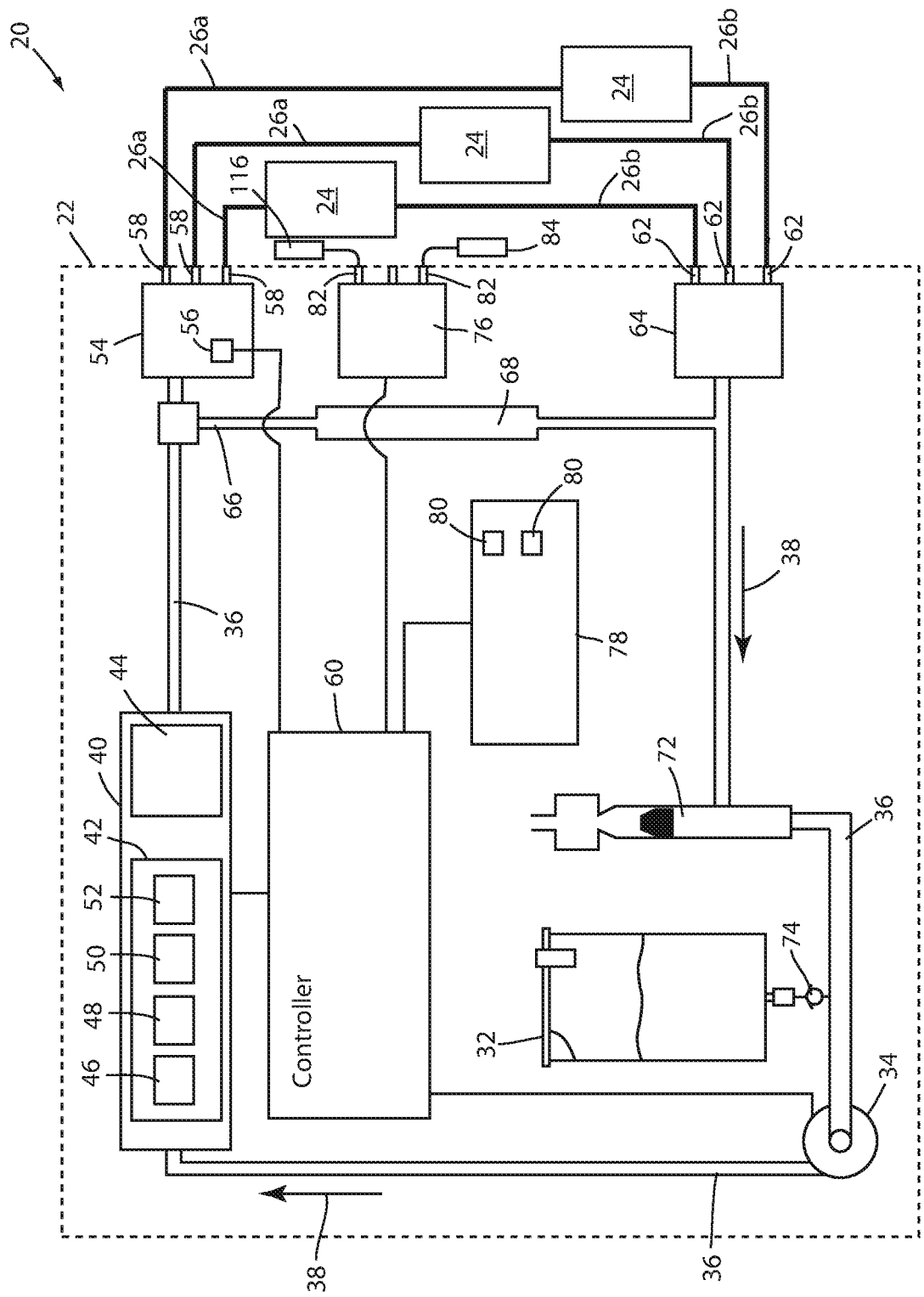
FIG. 3 is a block diagram of a first embodiment of the thermal control unit of FIG. 2.

As shown in FIG. 3, thermal control unit 22 includes a pump 34 for circulating fluid through a circulation channel 36. Pump 34, when activated, circulates the fluid through circulation channel 36 in the direction of arrows 38 (clockwise in FIG. 3). Starting at pump 34 the circulating fluid first passes through a heat exchanger 40 that adjusts, as necessary, the temperature of the circulating fluid. Heat exchanger 40 may take on a variety of different forms. In some embodiments, heat exchanger 40 is a thermoelectric heater and cooler. In the embodiment shown in FIG. 3, heat exchanger 40 includes a chiller 42 and a heater 44. Further, in the embodiment shown in FIG. 3, chiller 42 is a conventional vapor-compression refrigeration unit having a compressor 46, a condenser 48, an evaporator 50, an expansion valve (not shown), and a fan 52 for removing heat from the condenser. Other types of chillers and/or heaters may be used.

After passing through heat exchanger 40, the circulating fluid is delivered to an outlet manifold 54 having an outlet temperature sensor 56 and a plurality of outlet ports 58. Temperature sensor 56 is adapted to detect a temperature of the fluid inside of outlet manifold 54 and report it to a controller 60. Outlet ports 58 are coupled to supply hoses 26a. Supply hoses 26a are coupled, in turn, to thermal pads 24 and deliver temperature-controlled fluid to the thermal pads 24. The temperature-controlled fluid, after passing through the thermal pads 24, is returned to thermal control unit 22 via return hoses 26b. Return hoses 26b couple to a plurality of inlet ports 62. Inlet ports 62 are fluidly coupled to an inlet manifold 64 inside of thermal control unit 22.

Control unit 22 also includes a bypass line 66 fluidly coupled to outlet manifold 54 and inlet manifold 64 (FIG. 3). Bypass line 66 allows fluid to circulate through circulation channel 36 even in the absence of any thermal pads 24 or hoses 26a being coupled to any of outlet ports 58. In the illustrated embodiment, bypass line 66 includes an optional filter 68 that is adapted to filter the circulating fluid. If included, filter 68 may be a particle filter adapted to filter out particles within the circulating fluid that exceed a size threshold, or filter 68 may be a biological filter adapted to purify or sanitize the circulating fluid, or it may be a combination of both. In some embodiments, filter 68 is constructed and/or positioned within thermal control unit 22 in any of the manners disclosed in commonly assigned U.S. patent application Ser. No. 62/404,676 filed Oct. 11, 2016, by inventors Marko Kostic et al. and entitled THERMAL CONTROL SYSTEM, the complete disclosure of which is incorporated herein by reference.

The flow of fluid through bypass line 66 is controllable by way of a bypass valve 70 positioned at the intersection of bypass line 66 and outlet manifold 54 (FIG. 3). When open, bypass valve 70 allows fluid to flow through circulation channel 36 to outlet manifold 54, and from outlet manifold 54 to the connected thermal pads 24. When closed, bypass valve 70 stops fluid from flowing to outlet manifold 54 (and thermal pads 24) and instead diverts the fluid flow along bypass line 66. In some embodiments, bypass valve 70 may be controllable such that selective portions of the fluid are directed to outlet manifold 54 and along bypass line 66.

The incoming fluid flowing into inlet manifold 64 from inlet ports 62 and/or bypass line 66 travels back toward pump 34 and into an air remover 72. Air remover 72 includes any structure in which the flow of fluid slows down sufficiently to allow air bubbles contained within the circulating fluid to float upwardly and escape to the ambient surroundings. In some embodiments, air remover 72 is constructed in accordance with any of the configurations disclosed in commonly assigned U.S. patent application Ser. No. 15/646,847 filed Jul. 11, 2017, by inventor Gregory S. Taylor and entitled THERMAL CONTROL SYSTEM, the complete disclosure of which is hereby incorporated herein by reference. After passing through air remover 72, the circulating fluid flows past a valve 74 positioned beneath fluid reservoir 32. Fluid reservoir 32 supplies fluid to thermal control unit 22 and circulation channel 36 via valve 74, which may be a conventional check valve, or other type of valve, that automatically opens when reservoir 32 is coupled to thermal control unit 22 and that automatically closes when reservoir 32 is decoupled from thermal control unit 22 (see FIG. 2). After passing by valve 74, the circulating fluid travels to pump 34 and the circuit is repeated.

Controller 60 of thermal control unit 22 is contained within main body 30 of thermal control unit 22 and is in electrical communication with pump 34, heat exchanger 40, outlet temperature sensor 56, bypass valve 70, a patient temperature module 76, and a user interface 78. Controller 60 includes any and all electrical circuitry and components necessary to carry out the functions and algorithms described herein, as would be known to one of ordinary skill in the art. Generally speaking, controller 60 may include one or more microcontrollers, microprocessors, and/or other programmable electronics that are programmed to carry out the functions described herein. It will be understood that controller 60 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions in thermal control unit 22, or they may reside in a common location within thermal control unit 22. When physically distributed, the components may communicate using any suitable serial or parallel communication protocol, such as, but not limited to, CAN, LIN, Firewire, 1-squared-C, RS-232, RS-465, universal serial bus (USB), etc.

User interface 78, which may be implemented as a control panel or in other manners, allows a user to operate thermal control unit 22. User interface 78 communicates with controller 60 and includes controls 80 enabling a user to turn control unit 22 on and off, select a mode of operation, select a target temperature for the fluid delivered to thermal pads 24, select a patient target temperature, and control other aspects of thermal control unit 22. In some embodiments, user interface may include a pause/event control, a medication control, and/or an automatic temperature adjustment control that operate in accordance with the pause event control 66b, medication control 66c, and automatic temperature adjustment control 66d disclosed in commonly assigned U.S. patent application Ser. No. 62/577,772 filed on Oct. 27, 2017, by inventors Gregory Taylor et al. and entitled THERMAL SYSTEM WITH MEDICATION INTERACTION, the complete disclosure of which is incorporated herein by reference.

In those embodiments where user interface 78 allows a user to select from different modes for controlling the patient's temperature, the different modes include, but are not limited to, a manual mode and an automatic mode, both of which may be used for cooling and heating the patient. In the manual mode, a user selects a target temperature for the fluid that circulates within thermal control unit 22 and that is delivered to thermal pads 24. Control unit 22 then makes adjustments to heat exchanger 40 in order to ensure that the temperature of the fluid exiting supply hoses 26a is at the user-selected temperature.

Another one of the modes is an automatic mode. When the user selects the automatic mode, the user selects a target patient temperature, rather than a target fluid temperature. After selecting the target patient temperature, controller 60 makes automatic adjustments to the temperature of the fluid in order to bring the patient's temperature to the desired patient target temperature. In this mode, the temperature of the circulating fluid may vary as necessary in order to bring about the target patient temperature.

In order to carry out the automatic mode, thermal control unit 22 utilizes patient temperature module 76. Patient temperature module 76 includes one or more patient temperature probe ports (FIGS. 2 & 3) that are adapted to receive one or more conventional patient temperature probes 84. The patient temperature probes 84 may be any suitable patient temperature probe that is able to sense the temperature of the patient at the location of the probe. In one embodiment, the patient temperature probes are conventional Y.S.I. 400 probes marketed by YSI Incorporated of Yellow Springs, Ohio, or probes that are YSI 400 compliant. In other embodiments, different types of probes may be used with thermal control unit 22. Regardless of the specific type of patient temperature probe used in thermal control system 20, each temperature probe 84 is connected to a patient temperature probe port 82 positioned on control unit 22. Patient temperature probe ports 82 are in electrical communication with controller 60 and provide current temperature readings of the patient's temperature. In some embodiments, patient temperature probe ports 82 may be wireless receivers adapted to receive patient temperature readings from one or more wireless patient temperature probes 84.

Figure 4:
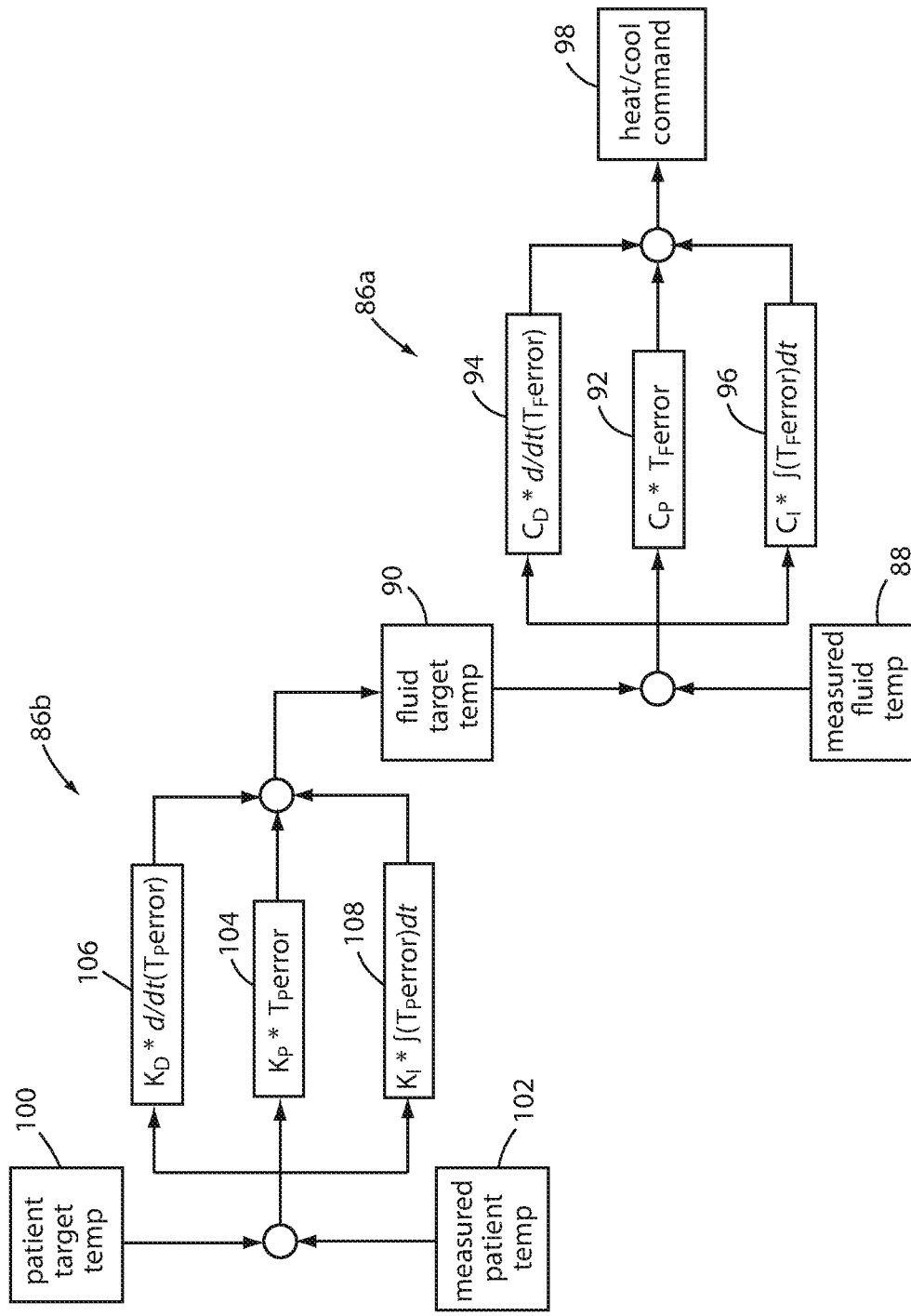
FIG. 4 is an illustrative control loop diagram that may be incorporated into at least one embodiment of the thermal control unit of FIG. 3.

FIG. 4 illustrates a pair of feedback loops 86a and 86b that are used in at least one embodiment of thermal control unit 22. Feedback loop 86a is used by controller 60 when thermal control unit 22 is operating in the manual mode and feedback loops 86a and 86b are both used by controller 60 when thermal control unit 22 is operating in the automatic mode. Feedback loop 86a uses a measured fluid temperature 88 and a fluid target temperature 90 as inputs. Measured fluid temperature 88 comes from outlet temperature sensor 56. Fluid target temperature 90, when thermal control unit 22 is operating in the manual mode, comes from a user inputting a desired fluid temperature using controls 80 of user interface 78. When thermal control unit 22 is operating in the automatic mode, fluid target temperature 90 comes from the output of control loop 86b, as discussed more below.

Control loop 86a determines the difference between the fluid target temperature 90 and the measured fluid temperature 88 ($T_F$error) and uses the resulting error value as an input into a conventional Proportional, Integral, Derivative (PID) control loop. That is, controller 60 multiplies the fluid temperature error by a proportional constant ($C_P$) at step 92, determines the derivative of the fluid temperature error over time and multiplies it by a constant ($C_D$) at step 94, and determines the integral of the fluid temperature error over time and multiplies it by a constant ($C_I$) at step 96. The results of steps 92, 94, and 96 are summed together and converted to a heating/cooling command at step 98. The heating/cooling command is fed to heat exchanger 40 and tells heat exchanger 40 whether to heat and/or cool the circulating fluid and how much heating/cooling power to use.

Control loop 86b which, as noted, is used during the automatic mode, determines the difference between a patient target temperature 100 and a measured patient temperature 102. Patient target temperature 100 is input by a user of thermal control unit 22 using controls 80 of user interface 78. Measured patient temperature 102 comes from a patient temperature probe 84 coupled to one of patient temperature probe ports 82 (FIG. 3). Controller 60 determines the difference between the patient target temperature 100 and the measured patient temperature 102 ($T_P$error) and uses the resulting patient temperature error value as an input into a conventional PID control loop (FIG. 4). As part of the PID loop, controller 60 multiples the patient temperature error by a proportional constant ($K_P$) at step 104, multiplies a derivative of the patient temperature error over time by a derivative constant ($K_D$) at step 106, and multiplies an integral of the patient temperature error over time by an integral constant ($K_I$) at step 108. The results of steps 104, 106, and 108 are summed together and converted to a target fluid temperature value 90. The target fluid temperature value 90 is then fed to control loop 86a, which uses it to compute a fluid temperature error, as discussed above.

It will be understood by those skilled in the art that although FIG. 4 illustrates two PID control loops 86a and 86b, other types of control loops may be used, including, but not limited to, a single control loop or more than two control loops. As other examples, loops 86a and/or 86b can be replaced by one or more PI loops, PD loops, and/or other types of control equations. Controller 60 implements loops 86a and/or 86b multiple times a second in at least one embodiment, although it will be understood that this rate may be varied widely. After controller 60 has output a heat/cool command at step 98 to heat exchanger 40, controller 60 takes another patient temperature reading 102 and/or another fluid temperature reading 88 and re-performs loops 86a and/or 86b. The specific loop(s) used, as noted previously, depends upon whether thermal control unit 22 is operating in the manual mode or automatic mode.

Figure 6:
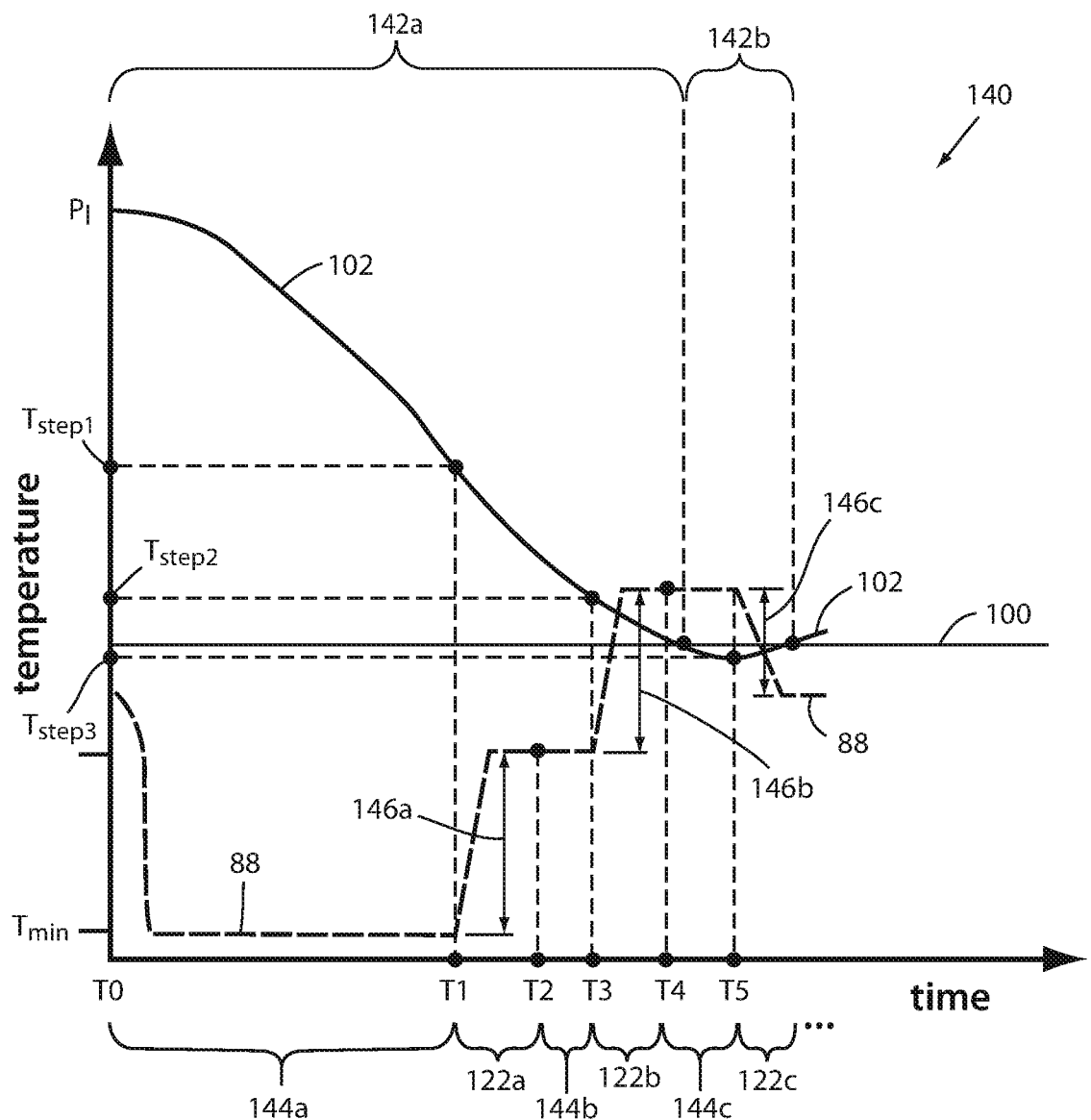
FIG. 6 is a graph of a patient target temperature, patient measured temperature, and fluid temperature illustrating a first example of the temperature control algorithm of FIG. 5.

It will also be understood by those skilled in the art that the output of the control loop 86a may be limited such that the temperature of the fluid delivered to thermal pads 24 by thermal control unit 22 never strays outside of a predefined maximum and a predefined minimum. The predefined minimum temperature, an example of which is shown in FIG. 6 and labeled $T_{min}$, is a temperature below which controller 60 does not lower the temperature of the circulating fluid. Minimum temperature $T_{min}$ is designed as a safety temperature and may vary. In some embodiments, it may be set to about four degrees Celsius, although other temperatures may be selected. The predefined maximum temperature, an example of which is not shown, is a temperature above which controller 60 does not heat the circulating fluid. The predetermined maximum temperature is also implemented as a safety measure and may be set to about forty degrees Celsius, although other values may be selected.

Figure 5:
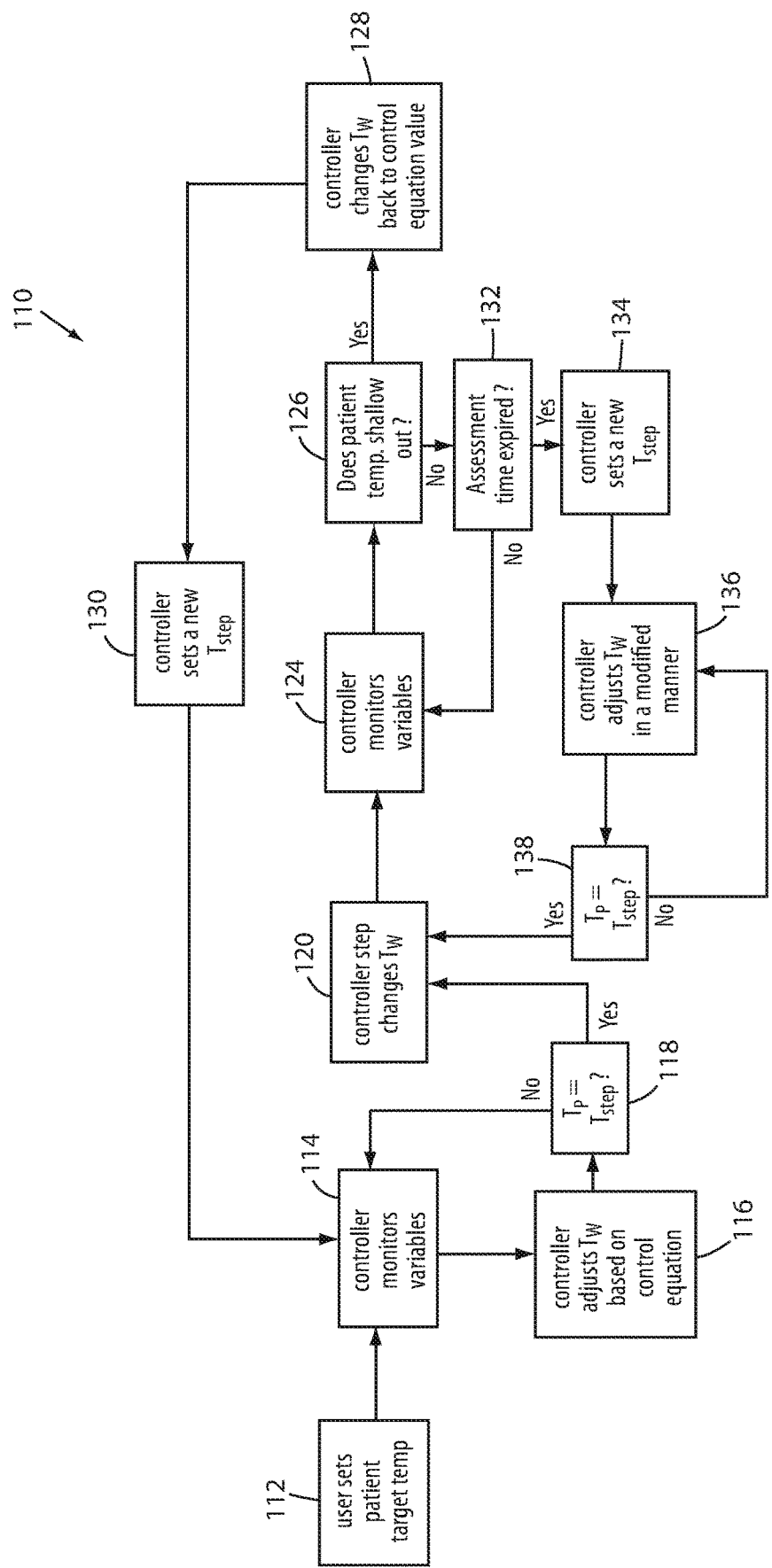
FIG. 5 is a flow diagram of a first temperature control algorithm that may be followed by a controller of the thermal control unit of FIG. 3.

FIG. 5 illustrates in more detail a temperature control algorithm 110 that controller 60 is adapted to implement in some embodiments of thermal control unit 22. Temperature control algorithm 110 is implemented when thermal control unit 22 is operating in the automatic mode—that is, when thermal control unit 22 is heating and/or cooling the temperature of the circulating fluid in order to automatically bring the temperature of the patient to a target temperature, and/or to maintain the patient temperature at the selected target temperature. Algorithm 110 begins at a temperature selection step 112 in which a user selects the patient target temperature 100.

After selecting the patient target temperature 100, controller 60 moves to step 114 where it takes readings of the basic variables used in controlling the patient's temperature. These basic variables include the fluid temperature 88 (measured by outlet temperature sensor 56), the patient temperature 102 (as measured by a patient temperature probe 84), and the patient target temperature 100 (as input by a user). In alternative embodiments, one or more additional readings may be taken, such as one or more measurements of the flow rate of fluid in circulation channel 36, a pump speed, a temperature of fluid returning into inlet manifold 64, the amount of heat removed from, or added to, the patient, and/or other variables.

After taking readings of the basic variables at step 114, controller 60 moves to step 116 where it implements the computations of control loops 86a and 86b (FIG. 4). That is, controller 60 determines the current error between the patient's measured temperature 102 and the patient target temperature 100 and feeds these variables into control loop 86b (FIG. 4). The output of control loop 86b is a target fluid temperature 90, which controller 60 compares against the current fluid temperature 88 to determine a fluid temperature error for use in control loop 86a. After determining the fluid temperature error, controller 60 performs steps 92-96 and outputs a heating/cooling command at step 98 to heat exchanger 40.

After control loops 86a and 86b have been completed once (or more than once), controller 60 moves onto step 118 (FIG. 5). At step 118 controller 60 determines whether a current patient temperature reading ($T_P$) taken from patient temperature probe 84 has reached, over moved past, a threshold temperature $T_{step}$. If the current patient temperature is not yet equal to the temperature threshold $T_{step}$, controller 60 returns to step 114 where it takes fresh readings of the patient temperature 102 and fluid temperature 88 for use in repeating step 114 in the manner described. If the current patient temperature is equal to the temperature threshold $T_{step}$ at step 118 (or moved past), controller 60 moves onto step 120, as will be discussed more below.

The temperature threshold $T_{step}$ used in step 118 is a temperature that is intermediate the patient target temperature 100 and the initial temperature of the patient ($P_I$; FIG. 6) when algorithm 110 starts. In some embodiments, $T_{step}$ is based on a specific patient temperature value, such as, but not limited to a patient temperature value that is approximately half way between the patient's initial temperature ($P_I$) and the patient's target temperature 100. Thus, for example, if the patient's initial temperature is thirty-seven degrees Celsius and the target patient temperature is thirty-three degrees Celsius, $T_{step}$ may be set equal to thirty-five degrees Celsius. Alternatively, $T_{step}$ may be a fixed value away from the target temperature 100, such as, but not limited to, one degree Celsius from the patient's target temperature 100. In still other embodiments, $T_{step}$ is not a temperature magnitude, but a slope magnitude that has to be met by the slope of recent patient temperature readings 102 before controller 60 moves onto step 120. In still other embodiments, $T_{step}$ is based on a combination of the slope of the patient temperature readings and also a specific patient temperature value. In these latter embodiments, controller 60 may look for a specific threshold slope to be achieved before then examining whether a specific temperature is achieved, or vice versa. Still other ways of combining a value and the rate of change of that value may be used.

If controller 60 determines at step 118 (FIG. 5) that the patient's current temperature is equal to $T_{step}$ or has moved past $T_{step}$, controller 60 moves to step 120. At step 120, controller 60 implements a step change in the fluid target temperature 90. That is, instead of controlling heat exchanger 40 using the target fluid temperature 90 derived from the output of control loop 86b, controller 60 selects a target fluid temperature 90 that is a marked departure from target fluid temperature 90 being output by control loop 86b in the moments immediately prior to step 120. Controller 60 then inputs the newly selected target fluid temperature 90 into control loop 86a and uses it to generate a heating/cooling command at step 98. Controller 60 continues to use the newly selected fluid target temperature 90 for a specific amount of time, referred to herein as an assessment time period 122, as will be discussed in greater detail below with respect to FIG. 6.

The new target fluid temperature 90 selected by controller 60 at time $T_{step}$ implements a step change in the temperature of the circulating fluid. In many embodiments, the new target fluid temperature 90 changes the immediately previous fluid target temperature by about five to ten degrees Celsius, although other magnitudes of change may be implemented. Further, after implementing the step change in the target fluid temperature 90 at time $T_{step}$, controller 60, when following the embodiment of algorithm 110 depicted in FIG. 5, maintains the newly selected fluid target temperature 90 for the assessment time period 122. That is, during assessment time period 122, controller 60 pauses using control loop 86b and simply inputs the new fluid target temperature 90 into control loop 86a. Alternatively, controller 60 could be configured to pause both control loops 86a and 86b during assessment time period 122 and send commands 98 generated by other means to heat exchanger 40 in order to expeditiously bring the fluid temperature 88 to the target fluid temperature 90.

Assessment period 122 begins at step 120 and lasts, in at least some embodiments, for a predetermined and fixed amount of time. This amount of time may vary from embodiment to embodiment, but in at least one embodiment, the fixed amount of time is in the approximate range of ten to twenty minutes. Time periods with other durations can, of course, be used. As will be discussed in greater detail below and with respect to FIG. 6, controller 60 determines when assessment period 122 ends at step 132.

After controller 60 implements the step change in target fluid temperature 90 at step 120 of algorithm 110 (FIG. 5), controller 60 moves to step 124. At step 124, controller 60 monitors the outputs from multiple sensors, including, but not limited to, the patient temperature readings 102 from patient temperature probe 84. Controller 60 may also monitor the fluid temperature readings 88 from temperature sensor 56 and/or other sensor readings. The monitoring of the sensor outputs at step 124 includes monitoring the slope of the patient temperature readings 102 from patient temperature probe 84. That is, controller 60 not only receives the patient temperature readings 102 from probe 84, it also stores them and calculates the slope of the readings 102 over time.

At step 126, controller 60 analyzes the monitored variables from step 124 and determines whether the patient temperature readings 102 have shallowed out (i.e. the absolute value of the slope of the patient temperature readings 102 over time has moved closer to zero) by more than a threshold. This determination is made both when the patient's current temperature readings are higher than the patient target temperature 100 and the patient is in the process of being cooled toward the patient target temperature 100, as well as when the patient's current temperature 102 is lower than the patient target temperature 100 and the patient is in the process of being warmed toward patient target temperature 100 (e.g. if thermal control unit 22 has overcooled the patient etc.). In some embodiments, the threshold is the same for when the patient is being warmed to target temperature 100 and when the patient is being cooled to target temperature 100. In other embodiments, the threshold for warming and cooling may be different.

Regardless of whether or not controller 60 uses the same threshold for warming or cooling, the threshold is chosen based on an assessment of how likely it will be for the patient to arrive at target temperature 100 within a desired time period if the step change implemented at step 120 is not reversed. In performing this analysis, controller 60 is configured to compare the rate of change of the patient's temperature readings 102 prior to implementing the fluid temperature step change (step 120) to the rate of change of the patient's temperature readings 102 after implementing the fluid temperature step change. This comparison examines how much the trajectory of the patient's temperature movement is influenced by the step change in the fluid temperature. If the trajectory change is too much (i.e. the absolute value of the slope drops too much), controller 60 concludes that it is unlikely for the patient to reach target temperature 100 within a desired time period without reversing the step change. If the trajectory change is not too much, controller 60 determines that the patient will likely reach target temperature 100 within an acceptable time frame without having to reverse the step change.

Controller 60 performs step 120 in order to determine if it can reduce earlier the heating/cooling for the particular patient being treated than it otherwise would were it to continue to follow the commands output by control loop 86b, and yet still reach the patient target temperature 100 in an acceptable amount of time. The reason for this determination is to help avoid overshoot. There can be a relatively lengthy lag time between the moment heat is applied or removed from the patient via thermal pads 24 and the moment the heat removal or addition affects the patient's core temperature. Further, this lag time varies from patient to patient, depending upon the morphology and physiology of a particular patient. Because this lag time varies from patient to patient, it can be difficult to tune the coefficients used in control loop 86b to bring a patient to a target temperature in an expeditious manner without causing overshoot in the patient's temperature. If a particular set of coefficients used with control loop 86b leads to changing the patient's temperature to a target temperature quickly and without overshoot for a first patient, those very same coefficients may cause a second patient to reach the same target temperature more slowly than desired, or overshoot the target temperature. In light of this patient-to-patient variability, controller 60 is configured to make adjustments to the heating/cooling commands that are tailored to the individual patient being treated. Controller 60 determines what these adjustments, if any, are to be during assessment period 122. As will be discussed more below, in some embodiments, the adjustments made by controller 60 after assessment period 122 include adjusting one of more of the coefficients of control loop 86b.

If controller 60 determines at step 126 that the rate of change of the patient's temperature 102 has shallowed out more than the threshold, controller 60 concludes that the step change in temperature will likely prevent the patient from reaching the patient target temperature 100 within an acceptable time period, and therefore reverses the step change. The rescission of the step change occurs at step 128 and involves abandoning the fluid target temperature 90 that was selected at 120, and instead restarting use of control loop 86b, which determines the fluid target temperature 90. The fluid target temperature 90 therefore goes through three stages in this example: it is initially determined by control loop 86b up until step 120; it is step changed by a fixed amount at step 120 and maintained thereat during assessment period 122; and it is returned back to being controlled by control loop 86b at step 128 (due to a greater-than-acceptable effect of the step change). It should be noted that when controller 60 reverses the step change at step 128, the fluid target temperature 90 generated by control loop 86b at that time may not be the same target fluid temperature 90 generated by control loop 86b in the moments immediately prior to assessment period 122. This is because the variables used in control loop 86b (e.g. patient temperature, fluid temperature, etc.) may, and likely have, changed over the course of assessment period 122.

After reversing the step change in the target fluid temperature at step 128, controller 60 proceeds to step 130 (FIG. 5) where it determines a new $T_{step}$ value. After determining the new $T_{step}$ value, controller 60 returns to step 114 and follows the previously described steps (including using the new $T_{step}$ value in the performance of step 118). The new $T_{step}$ value selected by controller 60 at step 130 is chosen to be at a temperature that is closer to the patient target temperature 100 than the previously selected $T_{step}$ value. Thus, for example, if the patient is being cooled from thirty-seven degrees Celsius to thirty-three degrees Celsius, and the original $T_{step}$ value was selected to be thirty-five degrees Celsius, the new $T_{step}$ value chosen at step 130 would be between thirty-three and thirty-five degrees Celsius. In some embodiments, the new $T_{step}$ value chosen at step 130 is partially or wholly based upon the degree to which the patient's temperature shallowed out during assessment step 126 (with the new $T_{step}$ being closer to the patient target temperature 100 the greater the shallowing of the rate of change of the patient temperature).

Although not illustrated in the diagram of FIG. 5, algorithm 110 is configured to limit the number of times step 130 is implemented during the course of bringing a patient's temperature 102 to the target patient temperature 100. The precise number to which controller 60 is limited may vary from embodiment to embodiment. Indeed, in at least one embodiment, step 130 is eliminated completely and controller 60 returns directly to step 114 after step 128 (and thereafter uses the equations of control loops 86a and 86b for the rest of the thermal cycle). In embodiments where the limit is non-zero, if controller 60 reaches step 128 again after the non-zero limit is reached, it skips step 130 and either returns to using control loop 86b until the target temperature 100 is reached, and/or takes other actions (e.g. selecting fluid target temperature that is not determined by control loop 86b). Once the patient reaches the target temperature 100, controller 60 may return to step 114 and resume using algorithm 110 in the manner previously described for the next thermal cycle. Such a resumption of algorithm 110 for a new thermal cycle may involve resetting $T_{step}$ still further, as will be discussed in greater detail below.

The term "thermal cycle" as used herein refers to the time periods between those moments when the patient's temperature 102 has reached the target patient temperature 100. Thus, in the case when the patient is being initially cooled from a normal body temperature to a lower temperature (e.g. 34 degrees Celsius), the first thermal cycle refers to the time period between the initial cooling of the patient and the moment when the patient reaches the target patient temperature 100. If there is overshoot of the patient's temperature below the target temperature 100, the second thermal cycle refers to the time period starting when the overshoot occurs until the time when the patient has been warmed back to the target temperature 100. If further overshoot occurs after, the third cycle refers to the time period when that further overshoot occurs until the patient's temperature is cooled back down to the target temperature 100. Further fluctuations of the patient's temperature after that lead to additional thermal cycles.

In light of the foregoing description of the thermal cycles, it is to be understood that controller 60 may be configured to utilize algorithm 110 for different numbers of thermal cycles in different embodiments. In one embodiment, controller 60 only utilizes algorithm 110 for the first cycle. In another embodiment, controller 60 only utilizes algorithm 110 for a specific number of cycles greater than one. In still other embodiments, controller 60 is configured to utilize algorithm 110 for a variable number of cycles, and in some of such embodiments, the number of cycles in which algorithm 110 is used is based upon how far away the patient's temperature is from the target temperature. For example, in some embodiments, if the patient's current temperature 102 is less than a degree away from target temperature 100, algorithm 110 is omitted. Still other variations are possible.

If controller 60 determines at step 126 that the rate of change of the patient's temperature has not shallowed out beyond the threshold, controller 60 proceeds to step 132 where it determines whether the assessment time period 122 has expired or not. If assessment time period 122 has not expired, controller 60 returns to step 124 and proceeds in the manner previously described. If assessment period 122 has expired at step 132, controller 60 moves to step 134. At step 134, controller 60 sets a new $T_{step}$ value. The setting of a new $T_{step}$ value at step 134, in some embodiments, is carried out in the same manner in which controller 60 sets a new $T_{step}$ value at step 130. In other embodiments, controller 60 is configured to use different rules or logic for setting the $T_{step}$ value at step 134. In those embodiments where controller 60 uses different logic or rules for setting the new $T_{step}$ value at step 134, controller 60 may select the new value of $T_{step}$ based on any one or more of the following: how far away from the target temperature 100 the patient's temperature 102 currently is; an estimate of how long it will take to reach the target temperature based on the rate of change of the patient's temperature; the previous value of $T_{step}$; the particular thermal cycle controller 60 is in; the current fluid temperature; and/or the relationship between the current fluid temperature and the patient target temperature 100.

Regardless of how controller 60 selects the new value for $T_{step}$ at step 134, controller 60 then moves to step 136 (FIG. 5). At step 136, controller 60 controls the temperature of the fluid (Tw=fluid temperature 88) to help bring the patient's temperature to the target temperature 100, and does so in a manner that is modified from the manner used in step 116. The particular modified manner in which controller 60 controls the fluid temperature at step 136 may vary from embodiment to embodiment. In one embodiment, controller 60 uses one or more control loops, such as control loops 86a and/or 86b, with at least one coefficient that is different from the coefficients used in step 116 (including, but not limited to, changing one or more non-zero coefficients to zero, or vice versa). In another embodiment, controller 60 maintains the fluid temperature at a constant temperature (such as, but not limited to, the step temperature of step 120) until controller 60 returns to step 120. In still another embodiment, controller 60 varies the fluid temperature 88 using control logic other than control loops 86a, 86b, or uses a modified version of these control loops.

Controller 60 continues to control the fluid temperature at step 136 until the patient's temperature (Tp=patient temperature 102) reaches the $T_{step}$ value set in step 134. Controller 60 determines whether $T_{step}$ has been reached at step 138. If it has not, controller 60 returns back to step 136 and continues to control the fluid temperature in a manner that brings the patient's temperature toward the patient target temperature 100. If it has, controller 60 moves to step 120 and proceeds in the manner previously described. Alternatively, in those embodiments where controller 60 is configured to only use algorithm 110 for a limited number of thermal cycles and in those instances where the limit has been reached, controller 60 may switch back to controlling the fluid temperature using the control loops 86a, 86b.

FIG. 6 illustrates a graph 140 of one illustrative situation in which algorithm 110 is implemented during first and second thermal cycles 142a and 142b. In the particular example shown therein, a patient is being cooled from an initial temperature $P_I$ at an initial time T0 to the patient target temperature 100. Readings of the patient temperature 102, as measured by patient temperature probe 84, are graphed over time as the patient undergoes cooling by thermal control system 20. Readings of the fluid temperature 88 are also graphed over time.

From the time between initial time T0 until time T1, controller 60 executes steps 114, 116, and 118 of algorithm 110. This time period will be referred to herein as a first time period 144a. First time period 144a ends at time T1, which refers to the time at which the patient's temperature 102 reaches $T_{step}$. More specifically, in the example of FIG. 6, T1 refers to the time that the patient's temperature 102 reaches $T_{step}$ for the first time (labeled as $T_{step\ 1}$). This value of $T_{step}$ refers to the value of $T_{step}$ used during the first iteration of step 118 (i.e. before controller 60 has ever moved from step 118 to step 120).

At time T1, first period 144a ends and controller 60 implements a first step change in the value of the target fluid temperature 90. Although FIG. 6 does not directly illustrate this step change, the magnitude of the step change is shown by reference number 146a, which corresponds to the jump in the fluid temperature 88 resulting from the step change in the target fluid temperature 90. The implementation of this first step change at time T1 corresponds to step 120 of algorithm 110 and marks the beginning of a first assessment period 122a.

First assessment period 122a last until time T2, which, in the illustrated example of graph 140, is the moment controller 60 moves from step 132 to step 134 of algorithm 110. It will be understood that in different situations, first assessment period 122 might end sooner than what is shown in FIG. 6 if the slope of the patient's temperature bottoms out by more than the threshold. This excessive bottoming out is not shown in FIG. 6, but corresponds to the situation where controller 60 ends first assessment period 122a by moving from step 126 to step 128.

The ending of first assessment period 122a occurs at time T2 and begins another period of time referred to herein as second time period 144b. In the example shown in FIG. 6, controller 60 is executing steps 136 and 138 of algorithm 110 during second time period 144b. Further, in the specific example shown in FIG. 6, controller 60 has been configured to maintain a constant fluid temperature 88 during second time period 144b. As was described above, controller 60 may be configured to implement step 136 in different manners. If, for example, controller 60 switches to using one or more control equations (e.g. 86a, 86b) having one or more coefficients different from those used during first time period 144a, the graph of the fluid temperature 88 will look different from what is depicted in FIG. 6 and will show some variation during second time period 144b.

At some point during second time period 144b, controller 60 also computes a new $T_{step}$ value (step 134). This is referred to in the example of FIG. 6 as $T_{step2}$ and, as discussed above, may be determined (or preset) in a variety of different manners. Second time period 144b continues until the patient's temperature 102 reaches this new $T_{step}$ value ($T_{step2}$), which is shown to occur at time T3 in FIG. 6. At time T3, controller 60 returns to step 120 and performs a second step change. The magnitude of this second step change is reflected in the reference number 146b and may be the same or different from the magnitude 146a of the first step change. The second step change marks the beginning of a second assessment period 122b, which lasts until time T4. As with the first assessment period 122a depicted in FIG. 6, controller 60 finds no bottoming out of the slope of the patient's temperature beyond the threshold during second assessment period 122b. Accordingly, controller 60 moves from step 126 to 132 to 134 in algorithm 110, rather than from step 126 to 128, and does not reverse the second step change.

After second assessment period 122b ends, controller 60 sets yet another new value for $T_{step}$ ($T_{step3}$) at step 134 and moves into a third time period 144c. During time period 144c, controller 60 executes steps 136 and 138 of algorithm 110. As noted above, the particular manner in which controller 60 controls fluid temperature 88 during time period 144c (or any of the other time periods 144) may vary from embodiment to embodiment, as well as within a particular embodiment. In the example shown in FIG. 6, controller 60 maintains the fluid target temperature 90 at a constant temperature during third time period 144c.

During third time period 144c, the patient's temperature 102 arrives at the patient target temperature 100 and a new thermal cycle 142b begins. As noted above, controller 60 is configured in some embodiments to select a new value for $T_{step}$ in this situation and/or to re-set the limit (if there is one) on the number of step changes controller 60 is programmed to implement. Third time period 144c continues until the patient's temperature reaches the new $T_{step}$, at which point controller 60 moves to step 120. Controller proceeds from step 120 in the same manner previously described through one or more further assessment periods (e.g. 122c . . . ) and one or more additional periods 144 between the assessment periods 122.

It will be understood by those skilled in the art that FIG. 6 merely represent one example of the manner in which controller 60 might control the fluid temperature 88 and patient temperature 102 when executing algorithm 110, and that the content of graph 140 may change dramatically, particularly if controller 60 follows the step change rescission branch of algorithm 110 (i.e. step 128) and/or if controller 60 controls the fluid temperature 88 using a non-constant target temperature during time periods 144. Still other changes in the configuration of controller 60 may also influence graph 140, including, but not limited to, the magnitude of the step changes 146, the length of assessment periods 122, the reaction of the patient to the applied thermal therapy, the limits on the number of iterations of algorithm 110 in a given thermal cycle, etc.

It will be understood that a number of enhancements and modifications to algorithm 110 and/or thermal control unit 22 can be made. For example, in order to enable thermal control unit 22 to implement a step change in the temperature of the fluid 88 more quickly, thermal control unit 22 may be configured to selectively mix the residual fluid contained within reservoir 32 with the fluid circulating within circulation channel 36 at those moments when a step change is implemented and/or reversed. One example of a suitable construction for thermal control unit 22 that includes this functionality is disclosed in commonly assigned U.S. patent application Ser. No. 62/610,319 filed Dec. 26, 2017, by inventors Gregory S. Taylor et al. and entitled THERMAL SYSTEM WITH OVERSHOOT REDUCTION, the complete disclosure of which is incorporated herein by reference. When thermal control unit 22 is modified to include the ability to selectively mix the residual fluid from reservoir 32 with the circulating fluid, it may be further modified to include a heater and/or chiller adapted to control the temperature of the residual fluid inside reservoir 32 substantially independently of the temperature of the fluid circulating within channel 36. Such a reservoir heater/chiller is also disclosed in the aforementioned '319 application.

It will also be understood that $T_{step}$ may be modified from a patient temperature value to a time-based criterion. For example, instead of implementing a step change based on the patient's temperature 102 reaching a specific temperature (e.g. $T_{step}$), the step change can be triggered based on the amount of time passed since the present thermal cycle began, an estimated amount of time until the patient arrives at the target temperature 100, and/or any other time characteristics. Still other factors may be used in selecting $T_{step}$, whether time based or not. Such other factors include, but are not limited to, knowledge stored in a memory of thermal control unit 22 indicating how long it takes thermal control unit 22 to change the temperature of the fluid from one temperature to another, the rate at which heat is being added/removed from the patient, one or more measurements of the patient's peripheral temperature, and patient data (e.g. weight, height, etc.).

Algorithm 110 may also be supplemented and/or combined with any one or more of the algorithms disclosed in the aforementioned commonly assigned patent application Ser. No. 62/610,319. In one such modified embodiment, controller 60 is configured to first stop delivering fluid to the patient for an initial assessment period, and then implement the step change described herein during a subsequent assessment period. The cessation of fluid delivery during such an initial assessment period may be carried out in the manner described in the '319 application. If controller 60 determines during that initial assessment period that the rate of change of the patients' temperature has bottomed out, then no step change is initiated. If controller 60 determines during the initial assessment period that the rate of change has not bottomed out, controller 60 moves to algorithm 110 and implements a step change during the subsequent assessment period. This combination of using an initial assessment period in which the fluid temperature is not changed (but instead stopped), and potentially a subsequent assessment period in which the fluid is step changed, may lead to fewer step change reversals.

In addition to, or in lieu of, any of the aforementioned modifications, thermal control system 20 may also be modified to include any of the features of the thermal control units described in any of the following commonly assigned U.S. patent applications, the complete disclosures of all of which are incorporated herein by reference: (1) 62/610,327 filed Dec. 26, 2017, by inventors Gregory S. Taylor et al. and entitled THERMAL SYSTEM WITH PATIENT SENSORS; 62/610,362 filed Dec. 26, 2017, by inventor Gregory S. Taylor and entitled THERMAL SYSTEM WITH GRAPHICAL USER INTERFACE; 62/610,334 filed Dec. 26, 2017, by inventors Christopher J. Hopper et al. and entitled THERMAL CONTROL SYSTEM; 62/477,596 filed Mar. 28, 2017, by inventors Gregory S. Taylor et al. and entitled THERMAL SYSTEM; Ser. No. 15/820,558 filed Nov. 22, 2017, by inventors Gregory S. Taylor et al. and entitled THERMAL SYSTEM; and Ser. No. 14/282,383 filed May 20, 2014, by inventors Christopher J. Hopper et al. and entitled THERMAL CONTROL SYSTEM.

Various other alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A thermal control unit for controlling a patient's temperature, the thermal control unit comprising:
    a fluid outlet adapted to fluidly couple to a fluid supply line;
    a fluid inlet adapted to fluidly couple to a fluid return line;
    a circulation channel coupled to the fluid outlet and the fluid inlet;
    a pump for circulating fluid through the circulation channel from the fluid inlet to the fluid outlet;
    a heat exchanger adapted to add or remove heat from the fluid circulating in the circulation channel;
    a fluid temperature sensor adapted to sense a temperature of the fluid;
    a patient temperature probe port adapted to receive patient temperature readings from a patient temperature probe;
    a user interface adapted to receive a patient target temperature; and
    a controller in communication with the patient temperature probe port, the pump, the fluid temperature sensor, and the user interface, the controller adapted to send commands to the heat exchanger to control a temperature of the fluid during an initial time period; to implement a step change in the temperature of the fluid during a subsequent time period; to monitor a slope of the patient temperature readings during the subsequent time period; and to control the heat exchanger using a first control loop feedback mechanism during the initial time period, the first control loop feedback mechanism using a first set of coefficients and an error value defined as a difference between a current patient temperature reading and the patient target temperature.

2. The thermal control unit of claim 1 wherein the controller is further adapted to monitor a slope of the patient temperature readings prior to implementing the step change.

3. The thermal control unit of claim 2 wherein the subsequent time period lasts for a fixed amount of time.

4. The thermal control unit of claim 3 wherein the controller is adapted to maintain a substantially constant target fluid temperature during the subsequent time period.

5. The thermal control unit of claim 4 wherein the controller is adapted to reverse the step change if the slope of the patient temperature readings changes by more than a threshold during the subsequent time period.

6. The thermal control unit of claim 5 wherein the controller, after reversing the step change and after the patient temperature has moved closer to the patient target temperature, is adapted to implement a second step change in the temperature of the fluid.

7. The thermal control unit of claim 4 wherein, if the slope of the patient temperature readings does not change by more than a threshold during the subsequent time period, the controller is adapted to continue to maintain the substantially constant target fluid temperature after the subsequent time period.

8. The thermal control unit of claim 1 wherein, if the slope of the patient temperature readings does not change by more than a threshold during the subsequent time period, the controller is further adapted to control the heat exchanger using a second control loop feedback mechanism after the subsequent time period, the second control loop feedback mechanism using a second set of coefficients and the error value, the second set of coefficients including at least one coefficient having a value different from a corresponding coefficient value in the first set of coefficients.

9. The thermal control unit of claim 1 wherein the controller is adapted to determine whether or not to reverse the step change based upon changes in the slope of the patient temperature readings during the subsequent time period.

10. The thermal control unit of claim 1 wherein the controller is adapted to determine whether or not to reverse the step change by determining a likelihood of the patient temperature readings reaching the patient target temperature without reversing the step change.

11. The thermal control unit of claim 1 wherein the controller is adapted to implement the step change when the patient temperature readings reach a specific temperature, the specific temperature being defined with respect to the patient target temperature.

12. The thermal control unit of claim 11 wherein the controller is further adapted to implement a second step change at a moment occurring after the subsequent time period when the patient temperature readings reach a second specific temperature, the second specific temperature being closer to the patient target temperature than the specific temperature.

13. A thermal control unit for controlling a patient's temperature, the thermal control unit comprising:

a fluid outlet adapted to fluidly couple to a fluid supply line;

a fluid inlet adapted to fluidly couple to a fluid return line;

a circulation channel coupled to the fluid outlet and the fluid inlet;

a pump for circulating fluid through the circulation channel from the fluid inlet to the fluid outlet;

a heat exchanger adapted to add or remove heat from the fluid circulating in the circulation channel;

a fluid temperature sensor adapted to sense a temperature of the fluid;

a patient temperature probe port adapted to receive patient temperature readings from a patient temperature probe;

a user interface adapted to receive a patient target temperature; and a controller in communication with the patient temperature probe port, the pump, the fluid temperature sensor, and the user interface, the controller adapted to perform the following:

(a) during an initial time period, use a first control equation having a patient target temperature and a current patient temperature as inputs and a fluid target temperature as an output, use a second control equation having the fluid target temperature and a current fluid temperature as inputs and a command for controlling the heat exchanger as an output, and use the fluid target temperature output from the first control equation as one of the inputs to the second control equation;

(b) during an interim time period, generate a new fluid target temperature without using the first control equation and use the new fluid target temperature as an input to the second control equation;

(c) monitor a slope of the patient temperature readings during the interim time period; and (d) determine from the slope of the patient temperature readings whether to modify at least one of the first or second control equations or to resume using the first and second control equations without modification of the first and second control equations.

14. The thermal control unit of claim 13 wherein, if the slope of the patient temperature readings does not change by more than a threshold during the interim time period, the controller is adapted to modify the at least one of the first or second control equation, and if the slope of the patient temperature readings does change by more than the threshold during the interim time period, the controller is adapted to resume using the first and second control equations without modification.

15. The thermal control unit of claim 13 wherein the controller is further adapted to determine and record a slope of the patient temperature readings prior to the interim time period and to use the recorded slope when determining whether to resume using the first and second control equations without modification or to modify the at least one of the first or second control equations.

16. The thermal control unit of claim 13 wherein the interim time period lasts for a fixed amount of time.

17. The thermal control unit of claim 13 wherein the controller is adapted to maintain the new fluid target temperature at a substantially constant temperature during the interim time period.

18. The thermal control unit of claim 13 wherein the controller starts the interim time period when the patient temperature readings reach a specific temperature, the specific temperature being defined with respect to the patient target temperature.

19. The thermal control unit of claim 18 wherein the fluid target temperature output by the first control equation at an end of the initial time period has a first value, the new fluid target temperature differs from the first value by at least five degrees Celsius, and the controller is adapted to maintain the new fluid target temperature at a substantially constant value throughout the interim time period.

* * * * *